United States Patent [19]

Silverstein et al.

[11] Patent Number: 5,775,322

[45] Date of Patent: Jul. 7, 1998

[54] TRACHEAL TUBE AND METHODS RELATED THERETO

[75] Inventors: Fred E. Silverstein, Seattle; Robert N. Golden, Kirkland; Christopher P. Somogyi, Woodinville, all of Wash.

[73] Assignee: Lucent Medical Systems, Inc., Bellevue, Wash.

[21] Appl. No.: 669,763

[22] Filed: Jun. 27, 1996

[51] Int. Cl.$^6$ .................................................. A61M 16/00
[52] U.S. Cl. .................. 128/207.14; 128/200.26; 128/10; 128/899
[58] Field of Search .................. 128/207.14, 200.26, 128/207.15, 10, 11, 899, 903, 716; 604/264

[56] References Cited

U.S. PATENT DOCUMENTS

| | | | |
|---|---|---|---|
| 4,416,289 | 11/1983 | Bresler | 128/207.14 |
| 4,943,770 | 7/1990 | Ashley-Rollman et al. | 128/207.14 |
| 5,005,573 | 4/1991 | Buchanan | 128/207.14 |
| 5,045,071 | 9/1991 | McCormick et al. | 128/207.14 |
| 5,203,320 | 4/1993 | Augustine | 128/207.14 |
| 5,331,967 | 7/1994 | Akerson | 128/207.14 |
| 5,425,282 | 6/1995 | Golden et al. | 128/899 |
| 5,560,351 | 10/1996 | Gravenstein et al. | 128/200.26 |

*Primary Examiner*—Aaron J. Lewis
*Assistant Examiner*—V. Srivastava
*Attorney, Agent, or Firm*—Seed and Berry LLP

[57] ABSTRACT

There is disclosed a tracheal tube for insertion into the trachea of a patient. The tracheal tube includes a tube portion having a distal end, and a signal source associated with the tube portion at a predefined distance from its distal end. The tracheal tube is inserted into the trachea such that the signal source is immediately posterior to the patient's cricothyroid ligament. Methods related to confirming proper placement of the tracheal tube by detecting the signal source immediately posterior to the patient's cricothyroid ligament are also disclosed.

16 Claims, 5 Drawing Sheets

TRACHEAL TUBE AND METHODS RELATED THERETO

TECHNICAL FIELD

This invention is generally directed to a tracheal tube and, more specifically, to a tracheal tube having a signal source associated therewith at a predefined distance from its distal end.

BACKGROUND OF THE INVENTION

There are many instances in clinical medicine where verifying the placement of a medical tube within a patient is important. In the case of endotracheal and nasotracheal tubes (collectively referred to herein as "tracheal tubes"), correct placement is critical. Tracheal tubes are generally plastic tubes inserted through the mouth or nose of a patient, and into the trachea, to assist breathing. Placement of the tube can be difficult, often resulting in incorrect placement in the esophagus. Since tracheal tubes are often necessary to ensure that a patient's lungs receive oxygen, misplacement can have dire consequences.

Doctors and other caregivers presently rely on a variety of techniques to correctly place tracheal tubes. However, patient anatomies and medical conditions vary to such a degree that any given technique will not ensure successful placement in all patients. Further, the experience of the caregiver will vary, and less experienced caregivers often find it difficult to correctly place tracheal tubes. Once inserted, the caregiver must verify that the tracheal tube has been correctly placed in the trachea rather than the esophagus. To this end, the caregiver will look for certain indications, including measurements of specific gas concentrations, air flow and pressure levels.

Furthermore, even when correctly inserted into the trachea, the tracheal tube must offer a clear ventilation path to both lungs. If inserted too deeply, the tracheal tube may enter one of the two main stem bronchi (normally the right) and direct air flow to and from only one of the lungs. The tracheal tube may even block ventilation to one of the main stem bronchi. In addition, if not inserted to a sufficient depth, the tracheal tube may result in damage to the vocal chords, particularly upon inflation of the securing and sealing balloon commonly present on such tubes.

Accordingly, there is a need in the art for improved tracheal tubes which allow a caregiver to verify that the tube has been properly inserted into the trachea (as opposed to the esophagus), and inserted to a proper depth within the trachea (i.e., neither too shallow nor too deep). The present invention fulfills these needs, and provides further related advantages.

SUMMARY OF THE INVENTION

In brief, this invention discloses a tracheal tube which, after insertion into a patient, can be verified to be properly positioned in the trachea (rather than the esophagus), and can be verified to be inserted to a proper depth within the trachea.

The tracheal tube of the present invention comprises a tube portion suitable for insertion into the trachea of a patient, and includes a signal source associated with the tube portion at a predefined distance from the distal end of the tube portion. The distance of the signal source from the distal end of the tube portion is such that, when the signal source is positioned immediately posterior to the cricothyroid ligament or membrane, the distal end of the tube portion is at the correct depth within the trachea.

In the practice of this invention, the signal source is capable of being detected by the caregiver (either directly or by employing an appropriate detecting device) immediately posterior to the patient's cricothyroid ligament. Thus, a method of this invention includes insertion of the tracheal tube within the trachea of a patient, positioning of the tube such that the signal source lies immediately posterior to the patient's cricothyroid ligament, and detecting the signal source at that location.

By associating the signal source a predefined distance from the distal end of the tube portion, proper depth of tracheal tube insertion can be verified by locating the signal source immediately posterior to the cricothyroid ligament. In addition, if the tracheal tube is improperly positioned in the esophagus, the signal source is no longer detectable immediately posterior to the cricothyroid ligament. Thus, the caregiver can verify that the tracheal tube has been improperly positioned, and can correctly reposition the tracheal tube within the trachea.

These and other aspects of the present invention will be better understood upon reference to the following detailed description and accompanying drawings.

DETAILED DESCRIPTION OF THE INVENTION

Figure 1A:
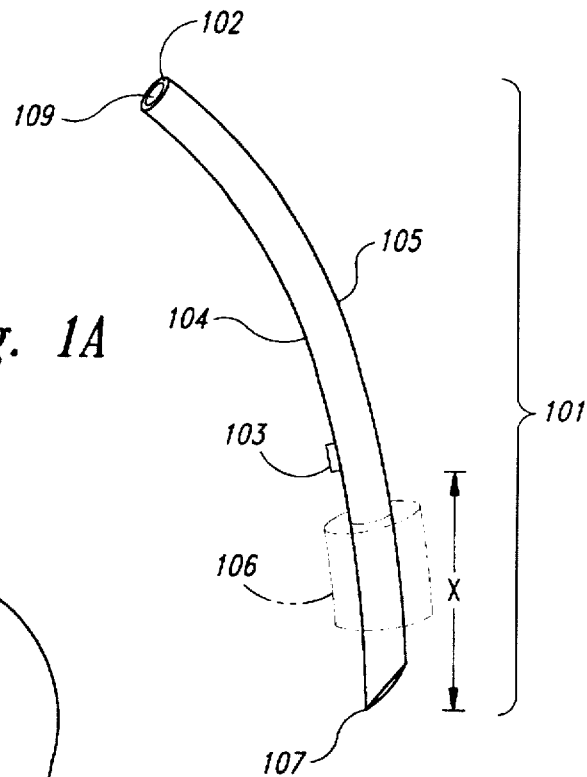
FIG. 1A illustrates a representative tracheal tube of this invention having a signal source associated a predefined distance "X" from the distal end.

As indicated above, the present invention is directed to a tracheal tube. As used herein, the term "tracheal tube" means any and all types of tubes which may be inserted into a patient's trachea, including (but not limited to) endotracheal tubes and nasotracheal tubes. The tracheal tube of this invention comprises a tube portion having a distal end and a proximal end, and a signal source associated with the tube portion a defined distance from its distal end. As used herein, the term "associated with" means permanently or removably affixed to the tube portion.

The tube portion of the tracheal tube may have an interior channel running from the proximal end to the distal end to permit air and/or other gases or fluids to travel through the tube portion. Furthermore, the tube portion has an anterior side and a posterior side. When inserted into the trachea of a patient, the anterior side of the tube portion is the side closest to the front or chest of the patient, while the posterior side is closest to the back of the patient.

To fully appreciate the tracheal tube of the present invention, particularly the necessity of associating the signal source a predefined distance from the distal end of the tube portion, a brief overview of the anatomy of the trachea and associated tissue is helpful. In very general terms, the trachea is the air passage that leads from the mouth to the lungs, while the esophagus is directly behind (i.e., posterior to) the trachea and leads to the stomach. The cricothyroid ligament is a section of tissue located in front of (i.e., anterior to) the trachea, between the thyroid cartilage and the cricoid cartilage. This ligament is the typical site of a tracheotomy, which is a procedure wherein a patient is given an emergency airway, bypassing the mouth and nose. The cricothyroid ligament is located a short distance below the surface of the skin just posterior to the thyroid cartilage, regardless of most anatomical variations. The vocal chords are located along the trachea between the cricothyroid ligament and the patient's mouth.

At the level of the cricothyroid ligament, the esophagus is posterior to the trachea (when viewing the patient from the front or anterior). The separation distance between the cricothyroid ligament and the esophagus is the outside diameter of the trachea, which is approximately 1–2 cm in most adults. A number of factors which are consistent from patient to patient make the cricothyroid ligament an ideal site for detection of a signal source associated with a tracheal tube. Such factors include, for example, the consistency in depth from the surface of the patient's skin to the cricothyroid ligament, the relatively fixed tracheal diameter in adult patients, the location of the esophagus relative to trachea at the cricothyroid ligament, and ease of locating the cricothyroid ligament relative to externally identifiable landmarks on the patient.

In most adults, the distance from the cricothyroid ligament to the carina of the trachea (i.e., the location where the trachea branches into the right and left main stem bronchi) is generally greater than about 5 cm. In children, this distance is less.

Regardless of the age of the intended patient, the tracheal tube of this invention has a signal source associated with the tube portion at a predefined distance from the distal end. This predefined distance is chosen such that, when the tracheal tube is properly positioned in the patient's trachea, the signal source is located immediately posterior to the cricothyroid ligament and the distal end of the tube portion is properly positioned above the carina. In the case of adults, the distance from the signal source to the distal end of the tube portion will generally range from about 3 to 5 cm, and is typically about 4 cm. For children, this distance will be less. Accordingly, the predefined distance from the signal source to the distal end of the tube portion depends on the age and/or relative size of the patient. To this end, the tracheal tubes of this invention may be manufactured for use on adults with a predefined distance from the signal source to distal end (such as 5 cm), and manufactured for children having a shorter predefined distance (such as 2 cm). The caregiver would thus select the appropriate tracheal tube for the specific patient.

When inserting the tracheal tube into the trachea, the caregiver inserts the same to a depth such that the signal source lies immediately posterior to the cricothyroid ligament. If inserted too deeply, the tracheal tube is correctly positioned by withdrawing the tube until the signal source is detected immediately posterior to the cricothyroid ligament. Conversely, if the tracheal tube is inserted to an insufficient depth, the tracheal tube is correctly positioned by inserting the tube further down the trachea until the signal source is detected immediately posterior to the cricothyroid ligament. Since the distal end of the tube portion is at predefined distance from the signal source, positioning of the tracheal tube in this manner ensures that its distal end is positioned at the proper depth. In other words, the tracheal tube is not inserted so deeply that full ventilation of both lungs is compromised, and is not inserted so shallowly that damage to the vocal chords occurs upon inflation of the securing and sealing balloon (i.e., the balloon is correctly positioned below the vocal chords).

In addition to positioning the tracheal tube at the proper depth within the trachea, correct placement within the trachea (as opposed to the esophagus) can also be verified. Since the esophagus is located behind or posterior to the trachea, the esophagus is separated from the cricothyroid ligament a distance equal to the outside diameter of the trachea. Thus, if the signal source is not detected immediately posterior to the cricothyroid ligament, the caregiver can determine that the tracheal tube has been improperly inserted into the esophagus rather than the trachea.

With regard to this aspect of the invention, the detection device indicates to the caregiver the depth of the signal source. If the signal source is detected too deep, the tracheal tube is incorrectly inserted into the esophagus. In the case of a normal adult, if the tracheal tube is improperly inserted in the esophagus, the signal source will be detected posterior to the skin over the cricothyroid ligament at a depth in excess of about 2 cm, and typically from 2 cm to 3½ cm (i.e., the cricothyroid ligament is approximately 1–1½ cm below the skin, plus the outside diameter of the trachea which is typically 1–2 cm). Accordingly, as used herein the phrase "immediately posterior to the cricothyroid ligament" means that the signal source is located within the trachea adjacent to the cricothyroid ligament.

In one embodiment of this invention, the tube portion has both an anterior side and a posterior side, and the signal source is associated with the anterior side a predefined distance from the distal end of the tube portion. As illustrated in FIG. 1A, tracheal tube (101) has tube portion (102) and signal source (103) associated therewith at a predefined distance "X" from distal end (107). Tube portion (102) has anterior side (104) and posterior side (105), as well as interior chamber (109) for the passage of air through the tube portion. Optional securing and sealing balloon (106) is located between signal source (103) and distal end (107). Signal source (103) is associated with anterior side (104) of tube portion (102).

Figure 1B:
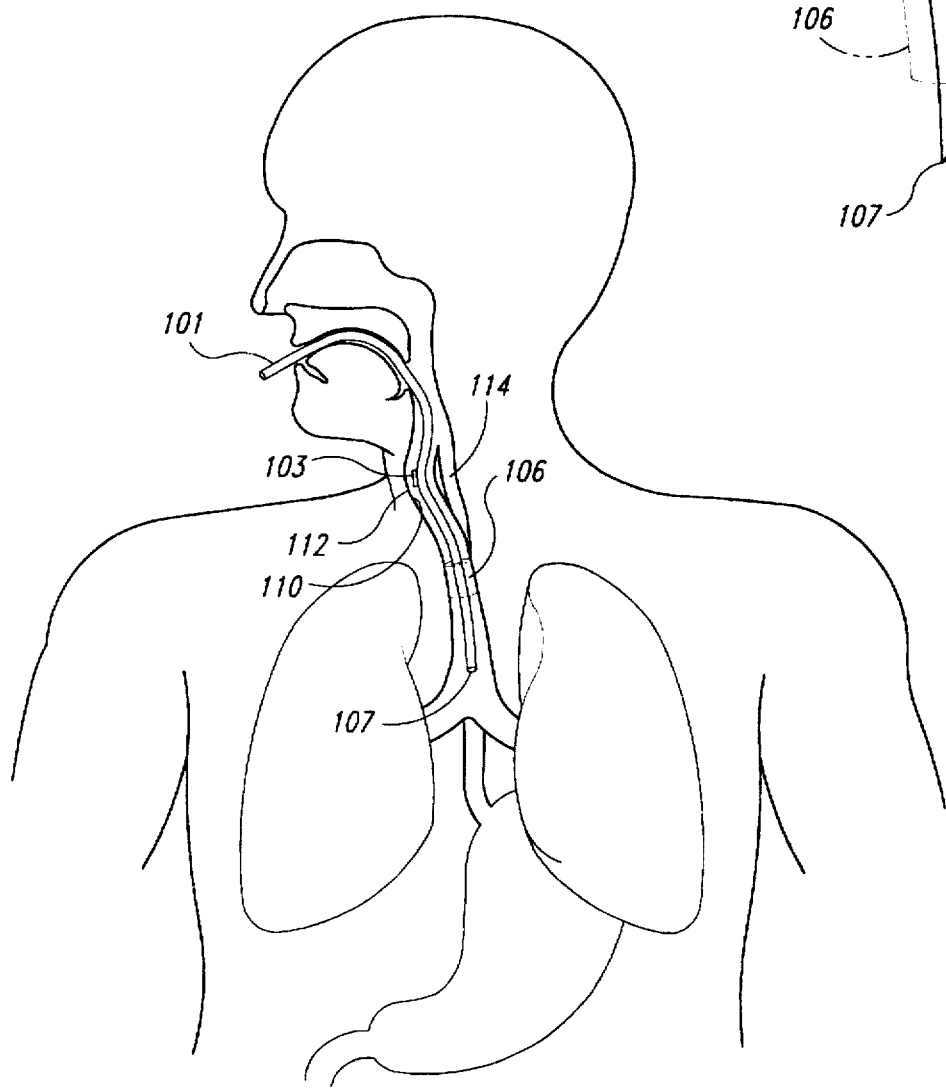
FIG. 1B illustrates the tracheal tube of FIG. 1A properly inserted into a patient's trachea.

When properly inserted into the trachea of a patient, the tracheal tube depicted in FIG. 1A is positioned as illustrated in FIG. 1B. Referring to FIG. 1B, tracheal tube (101) is located within trachea (110) with signal source (103) located immediately posterior to cricothyroid ligament (112). Optional securing and sealing balloon (106) is inflated below the cricothyroid ligament, and distal end (107) is properly positioned above the carina of the trachea. Esophagus (114) is depicted behind trachea (110), and separated from cricothyroid ligament (112) by the outside diameter of the trachea.

When properly inserted into the trachea, the anterior side of the tube portion is to the front of the patient, and the posterior side is to the back of the patient. Thus, the anterior side of the tube portion is closest in distance to the posterior of the cricothyroid ligament. By associating the signal source with the anterior side of the tube portion (as illustrated in FIG. 1A), the signal source is brought closer to the surface of the patient's skin directly under the cricothyroid ligament. Accordingly, in one embodiment of this invention, the signal source is associated with the anterior side of the tube portion.

Once inserted into the patient, the location of the signal source is detected by a suitable detection device. As used herein, the term "signal source" means any suitable device, substance and/or material that can be associated with the tracheal tube such that its presence immediately posterior to the cricothyroid ligament can be detected with an appropriate detection apparatus. Within the practice of this invention, a suitable signal source includes (but is not limited to) a permanent magnet, an electromagnet, a ferromagnetic material, an ultrasound reflector, emitter or absorber, an electromagnetic (such as radio or radar) reflector, emitter or absorber, an acoustic reflector, emitter or absorber, and a source of ionizing radiation such as a low-energy radioisotope.

The detection device will depend upon the type of signal source associated with the tracheal tube, and any device which can confirm that the signal source is immediately posterior to the cricothyroid ligament is suitable in the practice of this invention. Furthermore, it should be recognized that the detection device may, in some instances, be the caregiver. For example, when the signal source is an optical emitter (such as an LED), light emitted from the optical emitter may be directly visible to the caregiver through the skin directly over the cricothyroid ligament when the tracheal tube is properly positioned.

When the signal source is, for example, an ultrasound reflector or emitter, or a radar reflector, the detection device is an appropriate ultrasound or radar device which can indicate to the caregiver whether the signal source is immediately posterior to the cricothyroid ligament. Other suitable detection devices include, but are not limited to, radio transmitters and receivers, metal detectors and radiation detectors.

In a method of this invention, a caregiver inserts a tracheal tube into the trachea of a patient in need thereof. Proper placement of the tracheal tube is then confirmed by detecting the signal source immediately posterior to the cricothyroid ligament. If the signal source is not detected immediately posterior to the cricothyroid ligament, then the tracheal tube has either not been inserted to the proper depth, or has been improperly inserted into the esophagus. In either instance, the tracheal tube is re-positioned such that the magnet is detected immediately posterior to the cricothyroid ligament, thus verifying the proper insertion depth and location of the tracheal tube.

As mentioned above, the signal source is associated with the tube portion of the tracheal tube a predefined distance from the distal end. In a preferred embodiment, the signal source is associated with the anterior side of the tracheal tube as illustrated in FIG. 1A. In this embodiment, the signal source may be associated with the anterior side of the tracheal tube in any suitable manner, including (but not limited to) the use of an acceptable glue or tape to adhere the signal source to the tube portion. Furthermore, while FIG. 1A illustrates the signal source (such as a magnet) associated with the exterior surface of the tracheal tube, the signal source may be associated with an interior surface of the interior chamber, or may be integral to the tracheal tube itself.

Figure 2A:
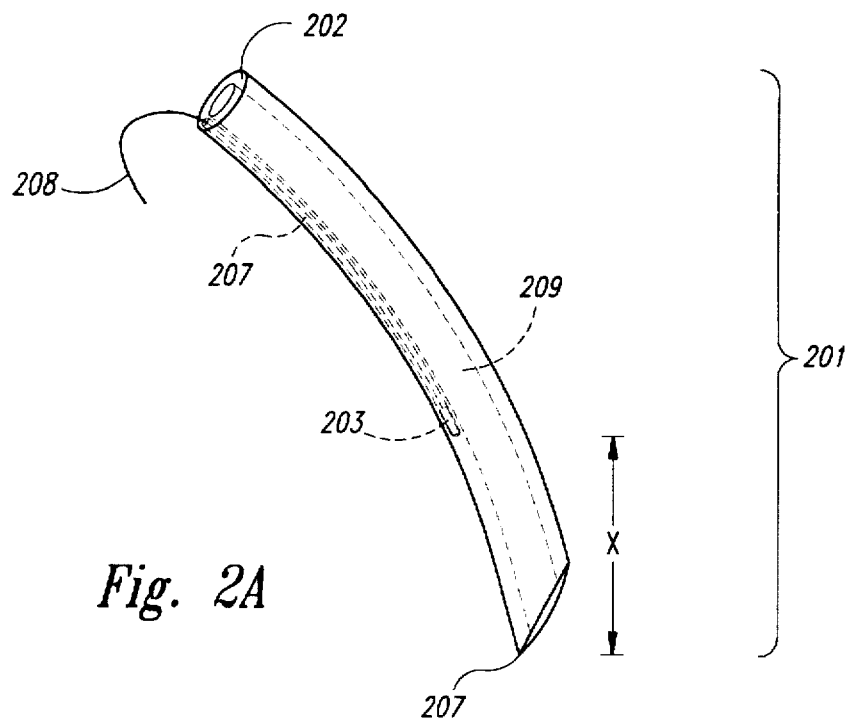
FIGS. 2A and 2B illustrate representative tracheal tubes of the present invention having a signal source removably associated a predefined distance "X" from the distal end of the tracheal tube.
Figure 2B:
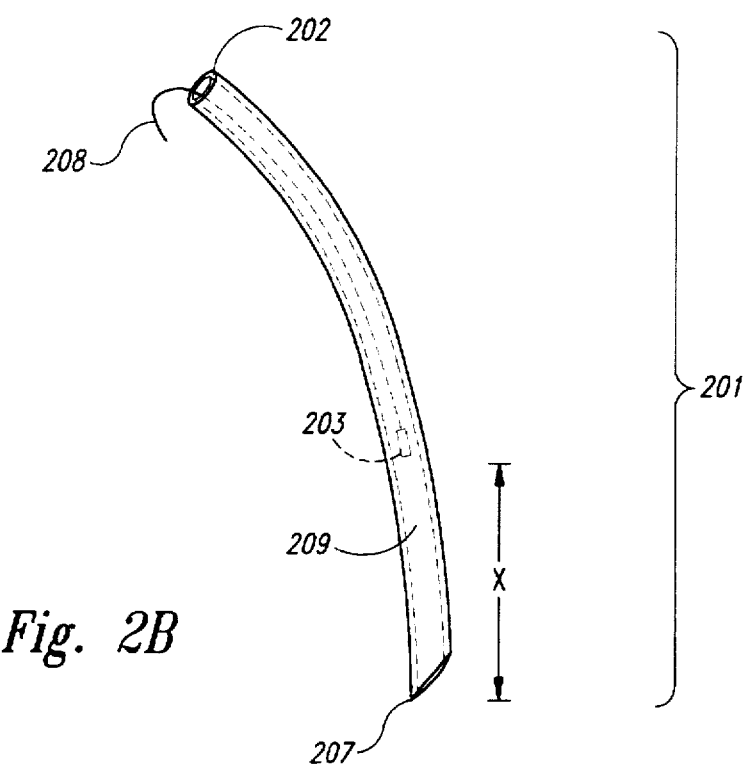

In an alternative embodiment, the signal source may be removably associated with the tracheal tube as illustrated in FIGS. 2A and 2B. Referring to FIG. 2A, signal source (203) is located within interior channel (207) of tube portion (202) of tracheal tube (201). Interior channel (207) is located within the side wall of tube portion (202), and separate from interior chamber (209) which permits the passage of air through the tracheal tube. Signal source (203) is attached to tether (208) to allow removal of the signal source after placement of the tracheal tube. Interior channel (207) terminates at a distance "X" from distal end (207).

In an alternative embodiment, the signal source may be located, for example, on a removable tether sized to fit around or within the tracheal tube during insertion, and capable of removal after proper placement of the tracheal tube. As illustrated in FIG. 2B, signal source (203) is attached to tether (208) and inserted into interior chamber (209) of tube portion (202). Tether (208) is sized such that signal source (203) is at distance "X" from distal end (207) of tracheal tube (201). Again, after positioning the tracheal tube, the signal source may be removed.

In one embodiment of this invention, the signal source is a magnet and the detection device is capable of detecting the location of the magnet when positioned immediately posterior to the cricothyroid ligament. A number of suitable magnet materials may serve this purpose, including ferromagnets, rare-earth magnets and electromagnets. In a preferred embodiment, the magnet is a permanent magnet and thus requires no power source. Suitable permanent magnets include rare earth magnets such as samarium cobalt and neodymium iron boron, both of which generate high field strengths per unit volume. While magnets which generate a high field strength for their size are preferred, weaker magnets such as Alnico or ceramic may also be utilized.

Suitable magnets of this invention may be solid or non-solid magnets, and further may be rigid or non-rigid magnets. Non-rigid magnets include (but are not limited to) suspensions of magnetic particles, as well as malleable forms of magnetic material (such as a putty). Rigid magnets (both solid and non-solid) are available from a variety of sources, including Dexter Corp. (Fremont, Calif.). The magnet may be associated with the tracheal tube such that its magnetic dipole is oriented parallel to the longitudinal axis of the tracheal tube. In a preferred embodiment, the magnetic dipole of the magnet may be oriented transverse to the longitudinal axis.

Non-rigid magnets (both solid and non-solid) are generally comprised of a plurality of magnet particles contained within a suspension or slurry, or within a more solid, but malleable, substance. Suitable suspension or slurries include (but are not limited to) magnetic particles within a fluid such as oil, water, glycerin, alcohol, fluid polymers and the like, provided such suspensions or slurries possess a detectable magnetic dipole. More solid, yet malleable, magnets include magnetic particles within a putty, polymer, silicone, highly viscous liquid and the like. Suitable polymers include those that are solid at room temperature, but malleable at body temperature.

When non-rigid magnets are employed, they are typically confined within an appropriate enclosure. In the case of suspensions or slurries, such magnets are associated with the medical tube within a suitable enclosure such that the suspension or slurry does not leak or escape from the medical tube. More viscous non-rigid magnets, such as putties and the like, are less susceptible to leakage, but may still benefit from an appropriate enclosure.

In one embodiment, the signal source is a hollow magnet having an interior chamber, such as a hollow cylindrical magnet. Hollow magnets for use in this invention typically have a length ranging from about 0.75 mm to about 12 mm, and preferably from 1.5 mm to 6 mm. Alternatively, the length of the hollow magnet may be relatively short, yielding a thin magnet. For example, in the case of a hollow cylindrical magnet, the magnet may be in the form of a relatively flat, hollow ring magnet. In this embodiment, the hollow ring magnet may have a length or thickness typically ranging from about 0.1 mm to about 5 mm. In the practice of this invention, a single magnet or multiple magnets may be associated with a single tracheal tube.

Figure 3A:
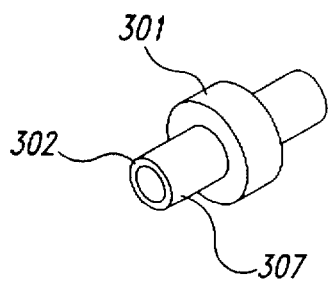
FIGS. 3A through 3D illustrate representative embodiments for associating a signal source with a tracheal tube of this invention.
Figure 3B:
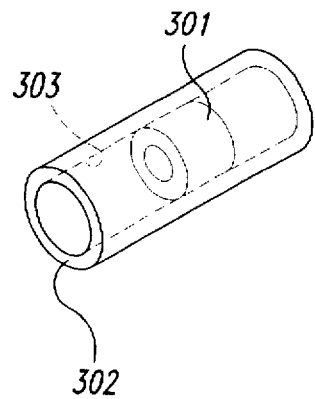
Figure 3C:
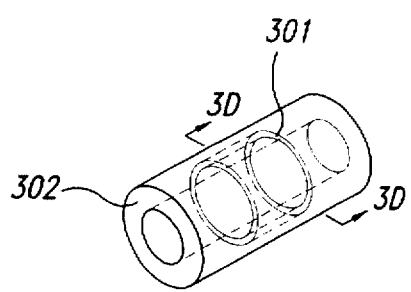
Figure 3D:
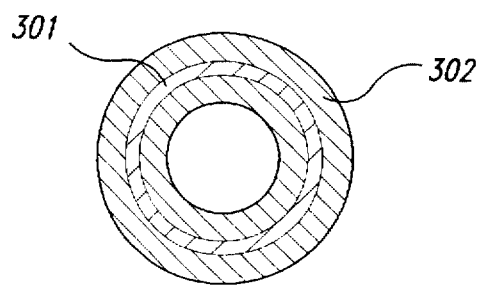

In this embodiment, the hollow magnet is associated with the tracheal tube such that air may pass through the interior chamber of the magnet. This may be achieved, for example, by associating the hollow magnet with the tracheal tube as illustrated in FIG. 3. Referring to FIG. 3A, hollow magnet (301) may be associated with tube portion (302) by locating the magnet around outside circumference (307) of the tube portion. Alternatively, hollow magnet (301) may be associated with interior circumference (303) of tube portion (302) as illustrated in FIG. 3B, or hollow magnet (301) may be integral to tube portion (302) as illustrated in FIGS. 3C and 3D.

Figure 4A:
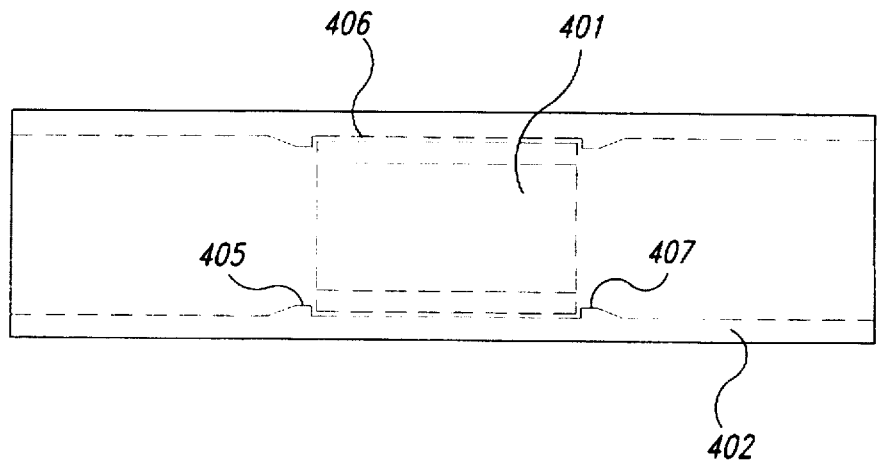
FIGS. 4A and 4B illustrate a signal source associated with an interior surface and an exterior surface, respectively, of a tracheal tube.
Figure 4B:
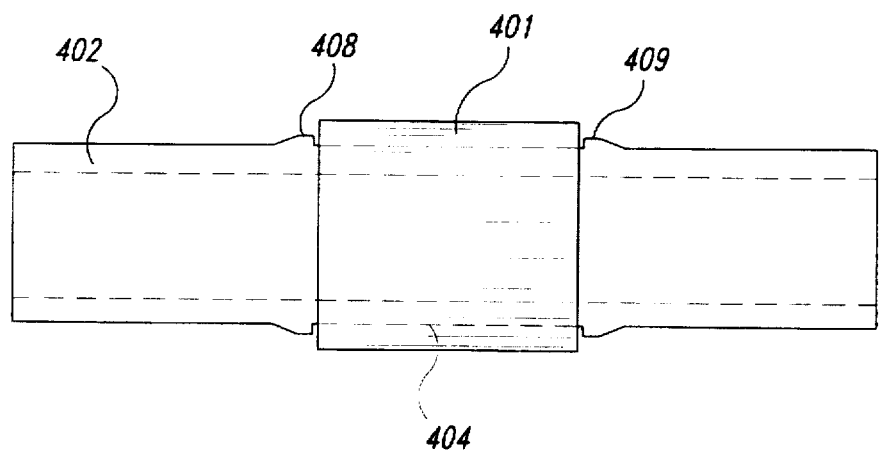

The hollow magnet may be associated with the tracheal tube by being affixed thereto, or may be confined to a specific location of the tracheal tube by, for example, locating the magnet within an appropriate magnet chamber or area. For example, referring to FIG. 4A, hollow magnet (401) may be located within an internal area of tube portion (402) defined by interior surface (406) and internally protruding ribs (405) and (407). Alternatively, as illustrated in FIG. 4B, hollow magnet (401) may be confined to an external area of tube portion (402) defined by exterior surface (404) and externally protruding ribs (408) and (409). In this embodiment, the length of the magnet, as well its exterior diameter in the case of FIG. 4A or its interior diameter in the case of FIG. 4B, are sized such that the magnet remains associated with the tube portion between the protruding ribs.

It should be recognized, however, that a variety of additional techniques can be employed to associate a signal source with a tracheal tube of this invention, as well as a variety of signal source configurations. For example, when the signal source is permanently affixed to the tracheal tube, such techniques include (but are not limited to) the use of suitable adhesives and/or tape, as well as incorporating the signal source in the manufacture of the tracheal tube such that it becomes integral to the tube itself.

As mentioned above, the signal associated with the tracheal tube may be detected using any suitable detection apparatus. In an embodiment where the signal source is a magnet, a suitable detection device is that disclosed in U.S. Pat. No. 5,425,382 and PCT Publication No. WO 95/08130, both to Golden et al. (which documents are incorporated herein by reference in their entirety, and collectively referred to as "the Golden et al. detection apparatus"). The Golden et al. detection apparatus detects the location of a magnet by sensing a static magnetic field strength gradient produced thereby. More specifically, that detection apparatus contains two static magnetic field strength sensors configured geometrically to null detection of ambient, homogeneous magnetic fields (e.g., the earth's field), while still detecting the magnetic field strength gradient produced by the magnet associated with the medical tube. The Golden et al. detection apparatus is an active, electronic instrument, and can detect the relatively small magnetic field strength gradient produced by the magnet at distances ranging from several centimeters to several decimeters. It also indicates the value of the gradient, thus allowing the user to accurately determine the location, orientation and depth (i.e., the distance from the detector) of the magnet.

In a preferred embodiment, the detection apparatus is capable of indicating the value of the gradient as both a magnitude and a polarity. To this end, the Golden et al. detection apparatus indicates to the user the direction of the magnet's dipole. Thus, by associating the magnet with the tracheal tube in a fixed and known orientation, the orientation of the magnet (and hence the tracheal tube) can be determined. For example, by associating the magnet with the tracheal tube such that the north pole is on the anterior side of the tracheal tube, and the magnet's south pole on the posterior side, the caregiver can determine whether the tracheal tube is properly oriented within the trachea with respect to its anterior/posterior positioning.

In a further embodiment, the magnet may be associated with the tracheal tube such that fluctuations in the magnetic dipole of the magnet indicates proper positioning within the trachea. When correctly placed, the tracheal tube of this invention resides in the trachea, providing an unobstructed path from the lower trachea to the outside air. Were a caregiver to apply rapid pressure to the diaphragm of the patient, resident air in the lungs would be forced out of the lungs and up the trachea. This force would result in a temporary increase in pressure within the interior chamber of the tracheal tube, and an associated increase in air speed therein. Thus, by associating the magnet such that its dipole fluctuates due to the increased air speed within the interior chamber of the tracheal tube, and sensing such fluctuations following an externally applied force to a patient's diaphragm, the caregiver can verify correct placement of the tracheal tube within the trachea (as opposed to the esophagus).

Alternatively, correct placement within the trachea can also be verified by associating the magnet such that its dipole fluctuates due to natural or artificial pleural ventilation. In this embodiment, the magnetic dipole fluctuation results from the passage of air into and/or out of the tracheal tube. Since placement in the esophagus would not result in such ventilation, the caregiver can verify correct placement by detecting the dipole fluctuation.

Figure 5A:
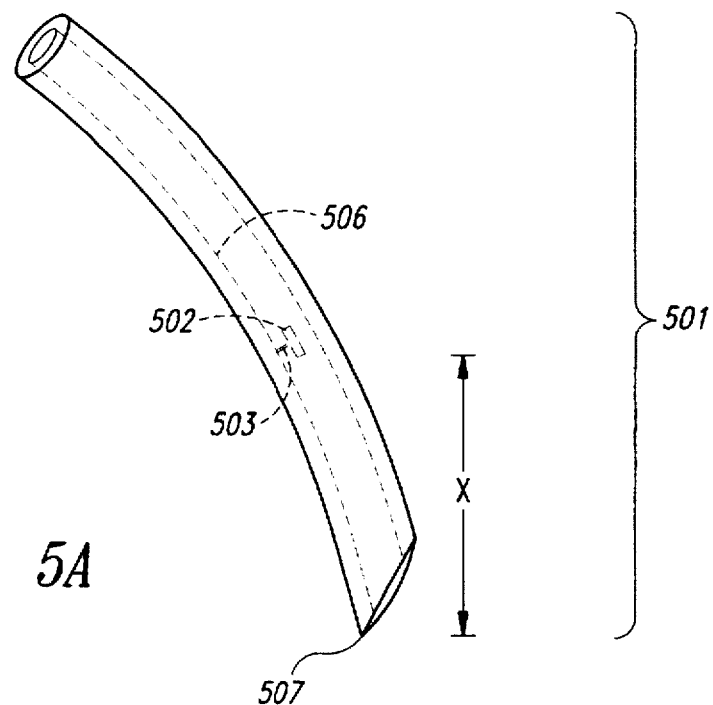
FIGS. 5A and 5B illustrate representative embodiments of tracheal tubes of this invention wherein a signal source is flexibly (FIG. 5A) and rotatably (FIG. 5B) associated with an interior surface of a tracheal tube.
Figure 5B:
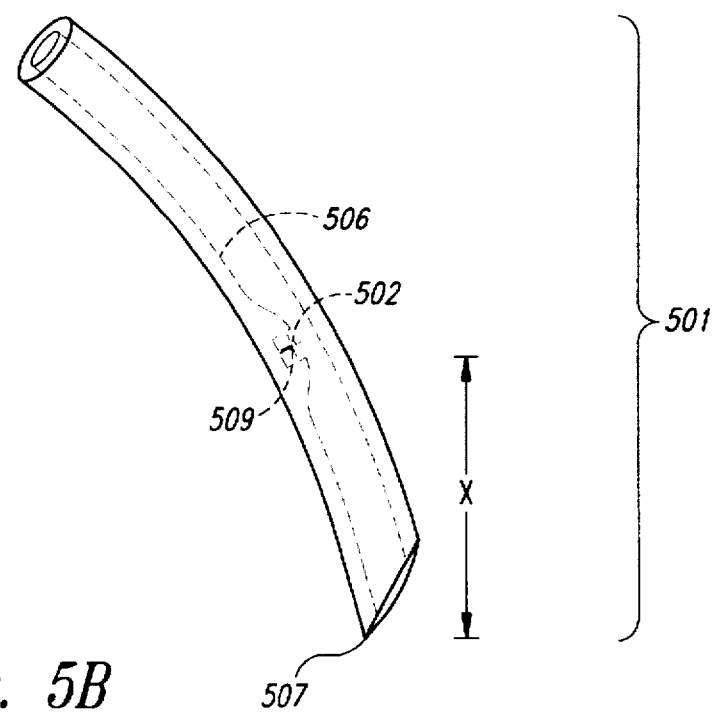

Accordingly, in another embodiment of this invention the magnet may be flexibly attached to the tracheal tube. Referring to FIG. 5A, magnet (502) is attached to flexible linker (503) which, in turn, is attached to internal surface (506) at a predefined distance "X" from distal end (507) of tracheal tube (501). Alternatively, as illustrated in FIG. 5B, magnet (502) is rotatably attached to internal surface (506) at a predetermined distance "X" from distal end (507) of tracheal tube (501). In this embodiment, the magnet is akin to a rotatable fan blade that rotates about axis (509) upon passage of air through the tracheal tube. By detecting the fluctuating dipole of the magnet associated with the tracheal tube, the caregiver can verify that the tracheal tube has been properly inserted into the trachea.

From the foregoing, it will be appreciated that, although specific embodiments of this invention have been described herein for purposes of illustration, various modifications may be made without deviating from the spirit and scope of the invention. Accordingly, the invention is not limited except by the appended claims.

We claim:

1. A tracheal tube for insertion into the trachea of a patient, comprising a tube portion having a distal end and a permanent magnet associated with the tube portion, wherein the permanent magnet is associated with the tube portion at a distance from the distal end such that, when the tube portion is inserted into the trachea of the patient and the permanent magnet is positioned immediately posterior to the patient's cricothyroid ligament, the distal end is positioned within the trachea at a proper depth.

2. The tracheal tube of claim 1 wherein the permanent magnet is permanently affixed to the tube portion.

3. The tracheal tube of claim 1 wherein the permanent magnet is removably affixed to the tube portion.

4. The tracheal tube of claim 1 wherein the permanent magnet is associated with the tube portion such that its magnetic dipole is parallel to a longitudinal axis of the tracheal tube.

5. The tracheal tube of claim 1 wherein the permanent magnet is associated with the tube portion such that its magnetic dipole is parallel to a transverse axis of the tracheal tube.

6. The tracheal tube of claim 1 wherein the tube portion has an anterior side and a posterior side, and wherein the permanent magnet is associated with the anterior side of the tube portion.

7. The tracheal tube of claim 1 wherein the tube portion has an internal surface and the permanent magnet is associated with the internal surface.

8. A method for confirming proper placement of a tracheal tube within the trachea of a patient, comprising inserting into the trachea a tracheal tube having a tube portion and a permanent magnet associated therewith, wherein the tube portion has a distal end and the permanent magnet is associated with the tube portion at a fixed distance from the distal end such that, when the permanent magnet is positioned immediately posterior to the patient's cricothyroid ligament, the distal end is positioned to permit ventilation of both lungs;

positioning the tracheal tube such that the permanent magnet is immediately posterior to the patient's cricothyroid ligament, and detecting the permanent magnet immediately posterior to the patient's cricothyroid ligament.

9. The method of claim 8 wherein the permanent magnet is permanently affixed to the tracheal tube.

10. The method of claim 8 wherein the permanent magnet is removably affixed to the tracheal tube.

11. The method of claim 10 wherein, after the step of detecting, the permanent magnet is removed from association with the tracheal tube.

12. The method of claim 8 wherein the detecting step detects the orientation of the magnet dipole of the permanent magnet.

13. A tracheal tube for insertion into the trachea of a patient, comprising a tube portion having a distal end and a permanent magnet associated with the tube portion, wherein the permanent magnet is associated with the tube portion at a distance from the distal end such that, when the tube is inserted into the trachea of a patient and the permanent magnet is positioned immediately posterior to the patient's cricothyroid ligament, the distal end of the tracheal tube is positioned within the trachea at a proper depth, and wherein the tube portion has an internal surface and the permanent magnet is rotatably affixed to the internal surface.

14. The tracheal tube of claim 13 wherein the magnet dipole of the permanent magnet rotates about an axis in response to air passing through the tracheal tube.

15. A tracheal tube for insertion into the trachea of a patient, comprising a tube portion having a distal end and a permanent magnet associated with the tube portion, wherein the permanent magnet is associated with the tube portion at a distance from the distal end such that, when the tube is inserted into the trachea of a patient and the permanent magnet is positioned immediately posterior to the patient's cricothyroid membrane, the distal end of the tracheal tube is positioned within the trachea at a proper depth, and wherein the tube portion has an internal surface and the permanent magnet is flexibly affixed to the internal surface.

16. The method of claim 15 wherein the magnetic dipole of the permanent magnet is displaced in response to air passing through the tracheal tube.

* * * * *

UNITED STATES PATENT AND TRADEMARK OFFICE
CERTIFICATE OF CORRECTION

PATENT NO.    : 5,775,322
DATED         : July 7, 1998
INVENTOR(S)   : Fred E. Silverstein, et al.

It is certified that error appears in the above-identified patent and that said Letters Patent is hereby corrected as shown below:

<u>Title page, item [56],</u>
The following should be added to the title page:
-- Related U.S. Application Data
Continuation of application No. 08/664,501, Jun. 17, 1996. --
The following should be added in the References Cited section on the Title page:
U.S PATENT DOCUMENTS
-- 5,257,636    11/1993      Steven J. White......... 128/897
   4,431,005    2/1984       William McCormick.... 128/656
   4,294,262    10/1981      Williams et al............ 128/726
   3,847,157    11/1974      Caillouette et al...........128/348

FOREIGN PATENT DOCUMENTS
   399 536 A1     11/1990       EPO
   29 22 240 A1   12/1979       Germany --.
References Cited, U.S. DOCUMENTS, "5,425,282 6/1995 Golden et al....128/899" should read -- 5,425,382 6/1995 Golden et al....128/899 --.
<u>Page 1,</u>
Line 3, the following should be inserted:
-- CROSS-REFERENCE TO RELATED APPLICATIONS
This is a continuation-in-part of Application No. 08/664,501, filed Jun. 17, 1996. --.

Signed and Sealed this

Second Day of October, 2001

Attest:

NICHOLAS P. GODICI
*Attesting Officer*   *Acting Director of the United States Patent and Trademark Office*